United States Patent [19]
Janevski

[11] Patent Number: 5,232,436
[45] Date of Patent: Aug. 3, 1993

[54] EXTENSION BLOCK FINGER SPLINT

[76] Inventor: Peter K. Janevski, 41552 Fawn Trail, Novi, Mich. 48375

[21] Appl. No.: 908,155

[22] Filed: Jul. 2, 1992

[51] Int. Cl.$^5$ .............................................. A61F 5/10
[52] U.S. Cl. .................................................... 602/22
[58] Field of Search ...................... 602/22, 21, 38, 16, 602/5; 128/77, 26; 273/54 B; 623/63, 64

[56] References Cited

U.S. PATENT DOCUMENTS

| | | | |
|---|---|---|---|
| 718,339 | 1/1903 | Graham | 602/16 |
| 3,039,460 | 6/1962 | Chandler. | |
| 3,692,022 | 9/1972 | Ewing. | |
| 3,994,493 | 11/1976 | Newman. | |
| 4,143,653 | 3/1979 | Wichman. | |
| 4,194,736 | 3/1980 | Loafman. | |
| 4,441,489 | 4/1984 | Evans et al.. | |
| 4,456,002 | 6/1984 | Barber et al.. | |
| 4,813,406 | 3/1989 | Ogle, II. | |

Primary Examiner—Richard J. Apley
Assistant Examiner—Beverly A. Meindl
Attorney, Agent, or Firm—Basile and Hanlon

[57] ABSTRACT

An extension block finger splint for treating proximal interphalangeal joint injuries is disclosed. The finger splint comprises a body including a first portion located distally of the proximal interphalangeal joint, the first portion comprising a curved member dorsally orientable about the distal interphalangeal joint. The body further includes a second portion hingedly and resiliently connected to the first portion at a predetermined an91e, the second portion located proximally of the proximal interphalangeal joint and comprising a curved member dorsally orientable about the finger adjacent the proximal interphalangeal joint. A mechanism, removably disposed on the body, is provided for increasing the predetermined angle by a predetermined increment. Further, a mechanism is provided for releasably securing the splint to the finger.

11 Claims, 2 Drawing Sheets

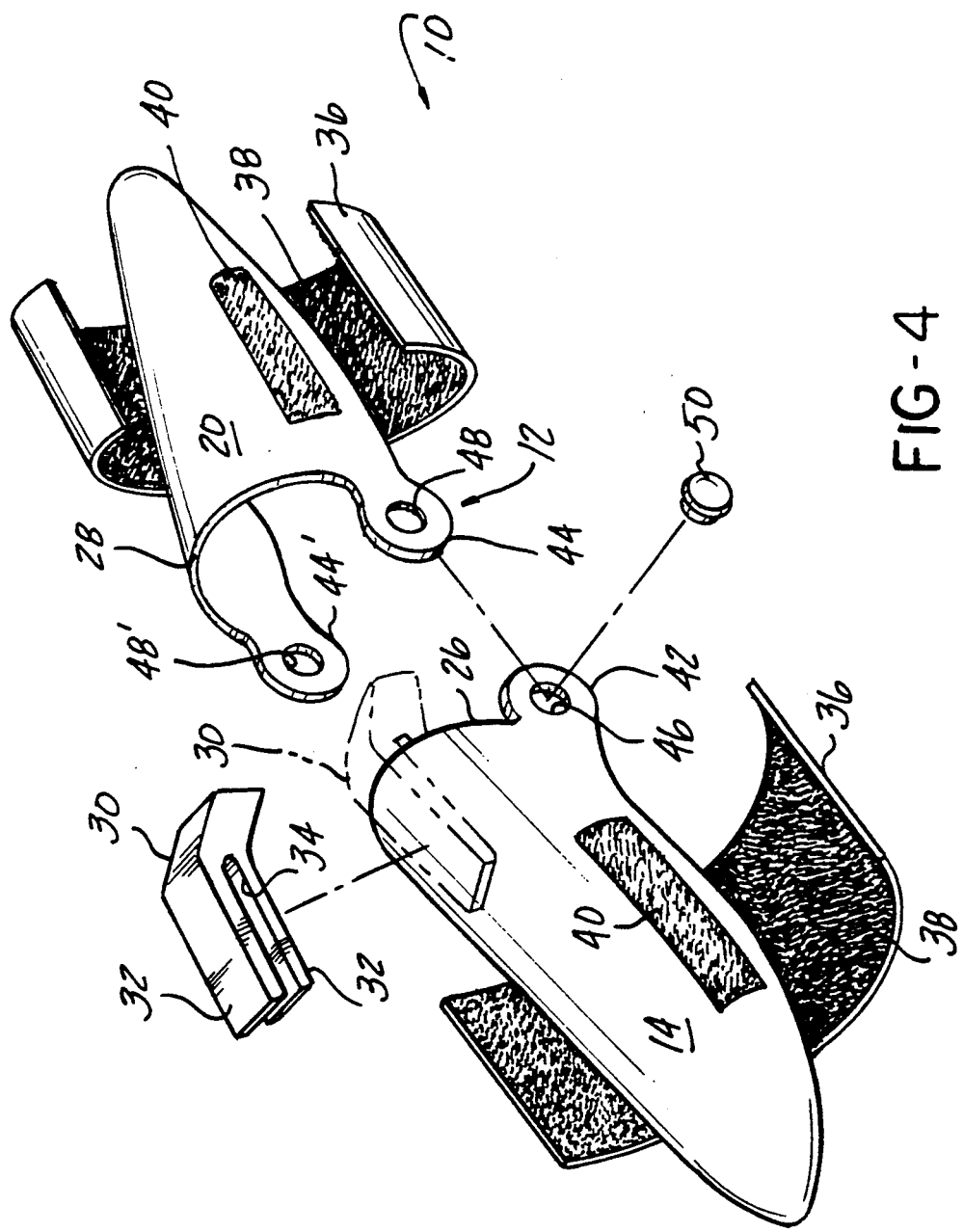

EXTENSION BLOCK FINGER SPLINT

BACKGROUND OF THE INVENTION

The present invention relates generally to orthopaedic splints, and more particularly to such a splint which is an extension block finger splint for treating proximal interphalangeal joint injuries.

Medical researchers are continually seeking newer, more efficient and better ways of treating digital injuries. The method of immobilizing a finger or the like in some type of splint has existed for centuries. However, rendering a limb or finger completely immobile during the entire course of healing has not proven to be medically desirable.

In particular, the generally recommended period of healing for an injury to the proximal interphalangeal joint of the finger is about six weeks, and total lack of movement of that joint during that period will tend to produce undesirable tendon contracture. Thus, splints have been developed which will keep this joint in flexion, while allowing restrained extension of that joint. This will relax the extensor tendon distally so that small movements of the joint can be made without separation of the tendon ends, thus allowing for exercise.

One such orthopaedic splint is disclosed in U.S. Pat. No. 4,441,489 issued to Evans. This reference discloses a splint which will hold the distal interphalangeal joint in hyperextension and the proximal interphalangeal joint in flexion, allowing restrained extension of the proximal interphalangeal joint. However, this reference, as well as various other known splint devices, are of a relatively complex structure. Further, they are formed of one integral piece, which is not always desirable. Still further, the angle at which the finger is splinted is not adjustable.

Thus, it is an object of the present invention to provide a finger splint which is angularly adjustable for staged joint motion. It is a further object of the present invention to provide such a splint which can be formed in two distinct yet interconnected portions, each of which can advantageously be exchanged for different shapes and sizes in order to more accurately fit a particular patient's digit. Still further, it is an object of the present invention to provide such a splint which is of a relatively simple construction, giving the advantage of quick, easy and inexpensive manufacture.

SUMMARY OF THE INVENTION

The present invention addresses and solves all the problems enumerated above. The present invention comprises an extension block finger splint for treating ligamentous injuries related to hyperextension or dislocations of the proximal interphalangeal joints. The finger splint comprises a body including a first portion located distally of the proximal interphalangeal joint, the first portion comprising a curved member dorsally orientable about the distal interphalangeal joint. The body further includes a second portion hingedly and resiliently connected to the first portion at a predetermined angle, the second portion located proximally of the proximal interphalangeal joint and comprising a curved member dorsally orientable about the finger adjacent the proximal interphalangeal joint. Means, removably disposed on the body, are provided for increasing the predetermined angle by a predetermined increment. Further, means are provided for releasably securing the splint to the finger.

BRIEF DESCRIPTION OF THE DRAWINGS

Other objects, features and advantages of the present invention will become apparent by reference to the following detailed description and drawings, in which:

FIG. 4 is an enlarged, exploded perspective view of the splint of the present invention.

DETAILED DESCRIPTION OF THE PREFERRED EMBODIMENTS

Figure 1:
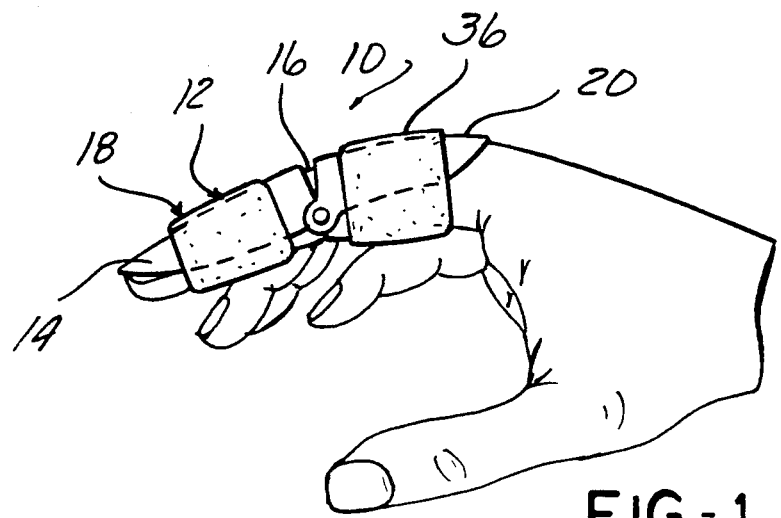
FIG. 1 is a perspective view showing the present invention in use on the user's finger.

Referring now to FIG. 1, the extension block finger splint of the present invention is designated generally as 10. Finger splint 10 is used for treating proximal interphalangeal joint injuries. Finger splint 10 comprises a body 12.

Figure 2:
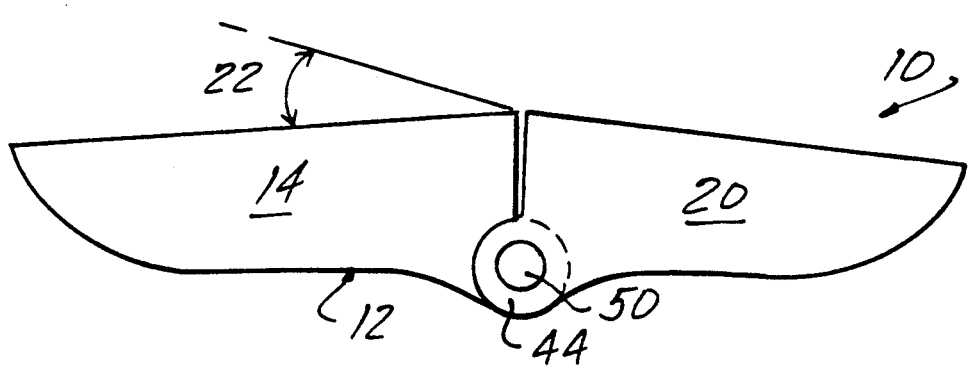
FIG. 2 is an enlarged side view of the splint of the present invention, shown without the releasable securing means.

Body 12 comprises a first portion 14 located distally of the proximal interphalangeal joint 16 of the finger, first portion 14 comprising a curved member (as best seen in FIG. 4) dorsally orientable about the distal interphalangeal joint 18 of the finger. Body 12 further comprises a second portion 20 hingedly and resiliently connected to the first portion 14 at a predetermined angle 22 (as best seen in FIG. 2). The second portion 20 is located proximally of the proximal interphalangeal joint 16 and comprises a curved member dorsally orientable about the finger adjacent the proximal interphalangeal joint 16. First and second portions 14, 20 each have mating edges 26, 28, respectively, adjacent the hinged connection.

Figure 3:
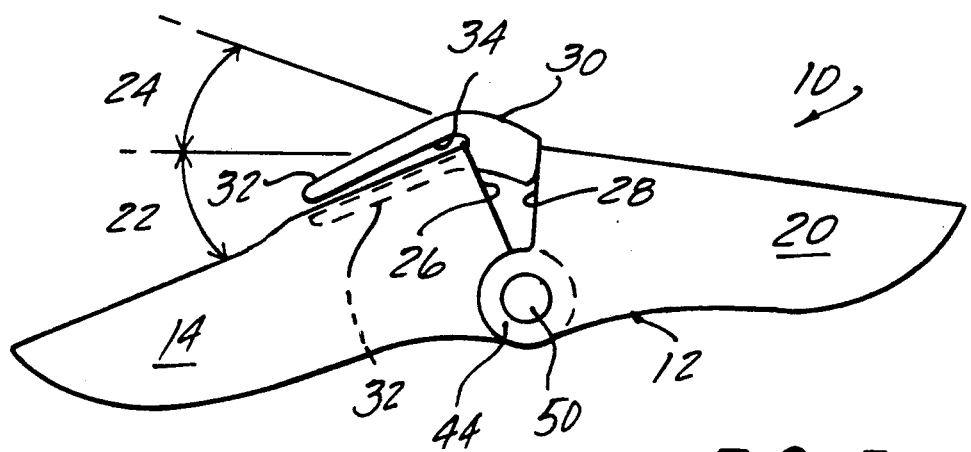
FIG. 3 is an enlarged side view of the splint of the present invention, shown with the removable extension clip in place, and without the releasable securing means.

Finger splint 10 further comprises means, removably disposed on body 12, for increasing the predetermined angle by a predetermined increment 24 (as best seen in FIG. 3). Predetermined angle 22 and predetermined increment 24 may be determined according to the amount or type of injury and the amount of flexion necessary for proper healing. In the preferred embodiment, predetermined angle 22 is 30° and the predetermined increment is also 30°.

The angle increasing means may comprise any suitable means, however, in the preferred embodiment, the angle increasing means comprises an extension clip 30 having two prongs 32 forming a slot 34 therebetween which receives one of the first portion and second portion mating edges 26, 28, respectively, and abuts against the other of the first portion and second portion mating edges 26, 28. In the preferred embodiment, slot 34 receives the first portion mating edge 26 and abuts against the second portion mating edge 28. Extension clip 30 may be selectively attached to splint 10 in order to provide staged joint motion.

Finger splint 10 further comprises means for releasably securing splint 10 to the finger. This releasable securing means 15 may comprise any suitable means. However, in the preferred embodiment, this securing means comprises a mating hook and loop strap 36, with the hooks 38 being on one of the body 12 and the strap 36, and the loops 40 being on the other of the body 12 and the strap 36. Any suitable hook and loop type arrangement may be used including a VELCRO TM brand fastener. Strap 36 is extendable about the finger and releasably connectable to body 12. Preferably, two straps 36 are utilized, one being extendable about the finger and connectable to the first portion 14, the other being extendable about the finger and connectable to second portion 20.

Second portion 20 may either be permanently, hingedly connected to first portion 14, or detachably, hingedly connected to first portion 14. In the preferred embodiment, first and second portions 14, 20 each have curved, mating edges 26, 28 adjacent the hinged connection and terminating in opposed projections 42 and 44, respectively. One projection 42 or 44 is adjacent one side of proximal interphalangeal joint 16, and the other projection 44' is adjacent the other side of proximal interphalangeal joint 16 (projections 42 being disposed in a similar manner). The projections 42, 44 each further define bores 46, 48 therethrough. A connecting pin 50 is receivable within the mating first portion bore 46 and second portion bore 48 on one side of the proximal interphalangeal joint 16, and a second connecting pin (identical to pin 50, but not shown) is receivable within the mating first portion bore and second portion bore 48' on the other side of the proximal interphalangeal joint 16. Pins 50 may either be permanently or removably received within the bores. If it is a removable connection, the splint 10 may be custom sized to a particular patient by selecting a properly sized first portion 14 for interconnection with a properly sized second portion 20.

It is to be understood that any suitable means for hingedly and resiliently connecting first portion 14 to second portion 20 is contemplated by the inventor as being within the scope of the present invention. It is further to be understood that splint 10 may be made by any suitable method out of any suitable material, including a durable polymeric material. The splint 10 may also come in various shapes and sizes, as desired.

While preferred embodiments of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. An extension block finger splint for treating proximal interphalangeal joint injuries, the finger splint comprising:
 a body, comprising:
  a first portion located distally of the proximal interphalangeal joint, the first portion comprising a curved member dorsally orientable about the distal interphalangeal joint; and
  a second portion hingedly and resiliently connected to the first portion at a predetermined angle, the second portion located proximally of the proximal interphalangeal joint and comprising a curved member dorsally orientable about the finger adjacent the proximal interphalangeal joint, wherein the first and second portions each have mating edges adjacent the hinged connection;
 means, removably disposed on the body, for increasing the predetermined angle by a predetermined increment, wherein the angle increasing means comprises an extension clip having two prongs forming a slot therebetween which receives one of the first portion and second portion mating edges and abuts against the other of the first portion and second portion mating edges; and
 means for releasably securing the splint to the finger.

2. The extension block finger splint as defined in claim 1 wherein the slot receives the first portion mating edge and abuts against the second portion mating edge.

3. The extension block finger splint as defined in claim 1 wherein the first and second portions are hingedly connected at a 30° angle, and wherein the extension clip provides another 30° increment of extension.

4. The extension block finger splint as defined in claim 1 wherein the releasable securing means comprises a mating hook and loop strap, with the hooks being on one of the body and the strap, and the loops being on the other of the body and the strap, the strap being extendable about the finger and releasably connectable to the body.

5. The extension block finger splint as defined in claim 4 further comprising two straps, one being extendable about the finger and connectable to the first portion, the other being extendable about the finger and connectable to the second portion.

6. The extension block finger splint as defined in claim 1 wherein the second portion is permanently, hingedly and resiliently connected to the first portion.

7. The extension block finger splint as defined in claim 1 wherein the second portion is detachably, hingedly and resiliently connected to the first portion.

8. The extension block finger splint as defined in claim 7 wherein the first and second portions each have curved, mating edges adjacent the hinged connection and terminating in opposed projections, one projection adjacent one side of the proximal interphalangeal joint, the other projection adjacent the other side of the proximal interphalangeal joint, the projections each further defining bores therethrough, and wherein a connecting pin is receivable within the mating first portion bore and second portion bore on one side of the proximal interphalangeal joint, and a second connecting pin is receivable within the mating first portion bore and second portion bore on the other side of the proximal interphalangeal joint.

9. An extension block finger splint for treating proximal interphalangeal joint injuries, the finger splint comprising:
 a body, comprising:
  a first portion located distally of the proximal interphalangeal joint, the first portion comprising a curved member dorsally orientable about the distal interphalangeal joint; and
  a second portion hingedly and resiliently connected to the first portion at approximately a 30° angle, the second portion located proximally of the proximal interphalangeal joint and comprising a curved member dorsally orientable about the finger adjacent the proximal interphalangeal joint, wherein the first and second portions each have mating edges adjacent the hinged connection;
 means, removably disposed on the body, for increasing the predetermined angle by a predetermined increment, wherein the angle increasing means comprises an extension clip having two prongs forming a slot therebetween which receives the first portion mating edge and abuts against the second portion mating edge, the extension clip providing approximately another 30° increment of extension; and means for releasably securing the splint to the finger.

10. The extension block finger splint as defined in claim 9 wherein the releasable securing means comprises a mating hook and loop strap, with the hooks being on one of the body and the strap, and the loops being on the other of the body and the strap, the strap being extendable about the finger and releasably connectable to the body.

11. The extension block finger splint as defined in claim 10, further comprising two straps, one being extendable about the finger and connectable to the first portion, the other being extendable about the finger and connectable to the second portion.

* * * * *

UNITED STATES PATENT AND TRADEMARK OFFICE
CERTIFICATE OF CORRECTION

PATENT NO. :     5,232,436
DATED       :     August 3, 1991
INVENTOR(S) :   Leland Davis It is certified that error appears in the above-identified patent and that said Letters Patent is hereby corrected as shown below:

In the abstract, line 9, please delete "an9le" and insert --angle--.

Column 2, line 64, please delete "15".

Signed and Sealed this

Eighth Day of March, 1994

*Attest:*

BRUCE LEHMAN

*Attesting Officer*    *Commissioner of Patents and Trademarks*